United States Patent [19]

Sung et al.

[11] 4,030,918

[45] June 21, 1977

[54] INDIUM CONTAINING DENTAL ALLOY POWDER

[75] Inventors: Pei Sung, Lawrenceville; Frederic James Schweder, Trenton, both of N.J.

[73] Assignee: Johnson & Johnson, New Brunswick, N.J.

[22] Filed: May 27, 1976

[21] Appl. No.: 690,496

[52] U.S. Cl. .............................. 75/134 B; 75/.5 R;
75/134 C; 75/134 T; 75/169; 75/173 C
[51] Int. Cl.² ..................................... C22C 30/00
[58] Field of Search ............ 75/.5 R, 134 B, 134 C, 75/134 N, 134 T, 173 C, 169

[56] References Cited

UNITED STATES PATENTS

| | | | |
|---|---|---|---|
| 2,456,593 | 12/1948 | Polak | 75/134 C |
| 3,440,039 | 4/1969 | Watson | 75/134 C |
| 3,495,972 | 2/1970 | Baum | 75/.5 R |
| 3,591,370 | 7/1971 | Denéreaz | 75/169 |
| 3,871,876 | 3/1975 | Asgar et al. | 75/169 |
| 3,975,192 | 8/1976 | Simpson | 75/169 |
| 3,980,472 | 9/1976 | Asgar et al. | 75/169 |
| 3,985,558 | 10/1976 | Simpson | 75/169 |

*Primary Examiner*—L. Dewayne Rutledge
*Assistant Examiner*—E. L. Weise

[57] ABSTRACT

A new dental alloy powder comprising homogeneous particles having a composition of 35 to 50 percent silver, 20 to 30 percent copper, 25 to 35 percent tin and 2 to 8 percent indium.

14 Claims, No Drawings

INDIUM CONTAINING DENTAL ALLOY POWDER

Amalgamatable dental alloys have been used for many years. These dental alloys, at least the conventional ones, contain from about 65 to 75 percent silver, 20 to 30 percent tin and up to 6 percent copper and 2 percent zinc. The conventional alloys, when amalgamated with mercury, form a substantial amount of gamma two phase which is corrosive and is detrimental to the final properties of fillings or restorations. In recent years new alloy compositions have been developed; basically, wherein the copper content is increased which in turn reduces the gamma two phase and improves the corrosion resistance of the amalgam.

Many conventional alloys contain non-uniform particles which are made from filing or grinding of the alloy ingot. In recent years alloys with spherical particles have been developed. Basically these alloys are made from an atomization process to form spherical particles. There is some indication that spherical particles can make amalgams as strong or stronger than those produced from filings. Most dental alloys contain a relatively high percentage of silver; that is, 65 percent or more and hence, are quite expensive. If the amount or percentage of silver is reduced, then the particles are treated so there is higher silver content on the outer surface of the particle than inside the particle in order to allow the alloy to be suitably amalgamatable. This further process step in the manufacture of the alloy powder produces increased costs in the production of the alloy powder.

In attempting to reduce the gamma two phase and hence, reduce the corrosion of amalgams made from alloy powders; it is often the case that the final alloy is not lathe cuttable and cannot be produced by a filing or grinding technique but must be atomized to produce a spherical particle.

What we have discovered is a new dental alloy that is amalgamatable, easily handled, and has excellent initial and long-term compressive strengths. Our new dental alloy has a lower percentage of silver than most alloys and hence, is economical. Furthermore, our new dental alloy is unexpectedly both grindable by standard lathe cutting techniques and may be formed into spherical particles by standard atomization techniques. In the process of making our new alloy, homogeneous particles are formed and there is no necessity for an added step to increase the percentage of silver on the outside surface area of the particle. Amalgams made using our new alloy have no gamma two phase and hence, excellent corrosion properties. Also, the amalgams made with our new alloys have low tarnishing qualities. Our new amalgamatable dental alloy comprises homogeneous particles having a composition of from 35 to 50 percent silver, 20 to 30 percent copper, 25 to 35 percent tin and 2 to 8 percent indium. Preferably, our new alloy is a powder of homogeneous particles of from 41 to 46 percent silver, 22 to 25 percent copper, 26 to 29 percent tin and 3 to 5 percent indium.

By including indium as part of the alloy, we unexpectedly obtain all of the desired strength advantages of the indium without having to be concerned with the particle size of the indium in order to obtain these advantages. In our new dental alloy, the powder comprises particles with each particle having a homogeneous composition and each particle having substantially the same composition. In the alloy, the silver to tin ratio will vary from about 1:1 to 2:1 whereas the tin to copper ratio will vary from about 5/6:1 to 1¾:1.

Generally our new alloys are in powder form having a particle size of less than 325 mesh. If desired our new alloys may be pelletized and produced in pellet form by pressing the alloy in a pharmaceutical pill machine. Our new alloy may also contain up to 2 percent zinc though it is preferred that the zinc be kept down to residual levels.

Our new alloys are amalgamatable with from about 46 to 58 percent mercury and preferably from about 48 to 52 percent mercury in mercury and powder combinations as is common with most alloys.

It is important in our new dental alloy to maintain the percent of silver within the 35 to 50 percent range and preferably within the 41 to 46 percent range. If more silver is present, our new alloy will not be effectively lathe cuttable. Furthermore, the higher the percentage of silver, the higher the cost of the alloy. If the amount of silver is reduced relow 35 percent, the final alloy powder is not readily amalgamatable and handleable. The amount of tin in our new alloy is maintained between the 25 to 35 percent range. If more than 35 percent tin is present the final amalgam will contain some gamma two phase and have poor corrosion properties. If less than 25 percent tin is used in our new alloy, the resultant alloy will not be lathe cuttable. If more than 30 percent copper is used the final alloy is very difficult to amalgamate and, of course, if the copper is reduced below the 20 percent level, you have excess tin present and will again form the undesirable gamma two phase. If less than 2 percent indium is included in our new alloy, you do not obtain the desired strength improvements applicable to the indium. The upper limit of indium to be used is controlled by cost factors along with increased setting times of amalgams formed from our new alloy. Higher percentages of indium increase the setting time of the amalgam.

It is believed the unexpected results of the present invention of a lathe cuttable, low silver content, gamma two free, homogeneous particle alloy are derived from the sliver, copper, tin, indium compositions. It is believed that the silver-tin compound of the $Ag_3Sn$ type, the copper-tin compound of the $Cu_3Sn$ type, along with the alloyed indium, unexpectedly produce the desirable results obtainable with the alloys of the present invention.

The following examples demonstrate preferred alloy compositions in accordance with the present invention. It should be noted that all percentages are given in weight percent throughout this specification.

The following test methods are used to determine the various physical properties of the dental amalgams produced in the following examples.

Gamma Two Determination

A Philips Electronic XRG-5000 X-ray generator with step diffractometer is used in determining the gamma two phase. A copper radiation is used for all studies. Polished amalgamated samples are used in all studies. The surfaces of the amalgamated sample are polished under cold water by using successively finer grit papers. The polished samples are scanned at 2 degrees ($2\theta$) per minute from 28° to 56° ($2\theta$). Particular attention is paid to the regions corresponding to the locations of the gamma two ($Sn_{7-8}Hg$) peaks.

Amalgam Set Time

This test is based on the principle that when the amalgam no longer can be reformed into a ball it has reached its set time. 0.60 grams of mercury and 0.60 grams of alloy powder are placed in a capsule and triturated for ten seconds with a Toothmaster, Model 300 Amalgamator. A stopwatch is started and any pestle used with the capsule removed. The capsule is replaced in the amalgamator and the mull button pressed to form a ball. One and one-half minutes is allowed to elapse and the mull button pressed again for one second. Every 30 seconds thereafter the mull button is pressed for one second until the sample crumbles for the first time. The first crumble occurs mid-way through the final set time. The mull button is pressed for three seconds to form a ball again. The mull button is pressed for one second every thirty seconds thereafter until the second ball crumbles. The elapsed time between the end of trituration and the crumbling of the ball the second time is recorded as the set time.

Amalgam Compressive Strengths 0.63 grams of mercury and 0.63 grams of alloy powder are placed in a capsule with a pestle and triturated for 10 seconds using a Toothmaster Amalgamator. The capsule is opened, the pestle removed, and the amalgam poured into a die cavity. A plunger is placed on top of the amalgam and 2000 pounds per square inch of pressure applied. The load is applied and released a number of times to compact and press the amalgam. Excess mercury is brushed away and the sample ejected from the die. The sample is four millimeters in diameter and eight millimeters in length. Samples made as described above are conditioned for one hour and 24 hours in an oven at 37° C. The resultant conditioned cylindrical sample is placed on its verticle axis in the compression cell of a compression testing machine and compressive strength tested. The compression testing machine used is an Instron Tester Model TMA1115.

Creep 0.63 grams of mercury and 0.63 grams of alloy powder are placed in a capsule with a pestle and triturated for eight seconds. The capsule is opened, the pestle removed and the amalgam placed in a die cavity. A plunger is placed in the cavity and 39.5 pounds of force applied to the amalgam. The force is applied and released a number of times. Excess mercury is brushed away and the sample ejected. A four millimeter diameter, eight millimeter long sample is produced. One hour after the end of trituration the ends of the cylindrical sample are planed at right angles to the axis. Seven days after trituration the cylinder specimen is tested. Twenty minutes prior to test the length of the cylinder specimen is measured. The cylindrical specimen is placed on its vertical axis between the top and bottom jaws of a creep tester. A 36.0 meganewton load (101.7 pounds) is applied to the specimen. Four hours after the load is applied, the sample is removed and the length measured. Creep is determined using the following calculation:

$$\text{Creep (\%)} = \frac{\text{length change between one and four hours} \times 100}{\text{original length}}$$

EXAMPLE I

Two different melts, hereinafter called melt A and melt B are made. Melt A comprises 87 grams of silver, 55 grams of tin, 48 grams of copper, two grams of zinc and seven grams of indium. Melt B comprises 84 grams of silver, 53 grams of tin, 46 grams of copper, two grams of zinc and 15 grams of indium. Both compositions are melted in induction furnaces at 1100° C. The final composition of melt A contains 45 percent silver, 29½ percent tin, 23.1 percent copper, 0.4 percent zinc and 2 percent indium. The final composition of melt B contains 43.1 percent silver, 27.7 percent tin, 22.4 percent copper, 0.4 percent zinc and 5.4 percent indium. Ingots are formed by pouring liquid metal into a 1 inch diameter graphite mold and quenching to room temperature in water. The resulting ingot is mounted on a mechanical lathe at a rotating speed of 80 rpms. A cutting tool at a 30° angle is used to cut the ingot at a feeding rate of 0.0015 inches per revolution. The filings are ball milled in a stainless steel jar with stainless steel balls for 2½ hours. The powder is screened through a 400 mesh screen. The −400 mesh powder is annealed at 350° C for 2½ hours. This procedure is followed for both melt A and melt B. Each of the powders is triturated in a Toothmaster Amalgamator with mercury and their properties measured. The results of the tests are given in the following table.

TABLE I

| | Melt A | Melt B |
|---|---|---|
| Particle Size | −400 mesh | −400 mesh |
| Powder to Mercury Ratio | 1:1 | 1:1 |
| Gamma Two Phase | No | No |
| Setting Time | 2½ to 3 minutes | 6 to 6½ minutes |
| One Hour Compression Strength | 26,423 psi | 23,028 psi |
| 24 Hour Compression Strength | 62,869 psi | 75,495 psi |

EXAMPLE II

Alloy powders of Example I are mixed with 25 percent silver-copper-eutectic powder containing 72 percent silver and 28 percent copper having a medium particle size of 28 microns. Each of the samples is triturated with mercury as previously described and their various physical properties measured and determined as given in the following table.

TABLE II

| | Melt A +25% silver-copper-eutectic | Melt B +25% silver-copper-eutectic |
|---|---|---|
| Particle Size of Melt | −400 mesh | −400 mesh |
| Powder to Mercury Ratio | 1:1 | 1:1 |
| Gamma Two Phase | No | No |
| Setting Time | ~ 3 minutes | ~ 4 minutes |
| One Hour Compression Strength | 31,734 psi | 23,379 psi |
| 24 Hour Compression Strength | 73,060 psi | 74,109 psi |

EXAMPLE III 436 grams of silver, 276 grams of tin, 248 grams of copper and 40 grams of indium are melted in an electric resistance furnace at 1100° C. The composition of the final melt contains 43.9 percent silver, 28.1 percent tin, 24.3 percent coper and 3.7 percent indium. The melt is cast in a 2 inch diameter graphite mold and cooled to room temperature in air. The 2 inch diameter cast ingot is mounted on a mechanical lathe and rotated at a speed of 78 rpm. A 30° molybdenum steel cutting tool at a tool feeding speed of 0.00075 inch per revolution is used to cut the ingot into fine filings. The filings are ball milled for 50 minutes in a stainless steel ball mill and screened through a 400 mesh screen. Portions of the −400 mesh powder are annealed at 100°, 200° and 300° C. Each of the various alloys is triturated with mercury and the resulting amalgams tested as described. The results of the test are given below.

TABLE III

| Annealing Temperature | 100° C | | 200° C | | 300° C | |
|---|---|---|---|---|---|---|
| Annealing Time in Minutes | 40 | 75 | 40 | 75 | 40 | 75 |
| Mercury to Powder Ratio | 1:1 | 1:1 | 1:1 | 1:1 | 1:1 | 1:1 |
| Setting Time/Minutes | 3 | 3 | 5 | 5½ | 7½ | 8 |
| One Hour Compression Strength PSI | 40.422 | 38.796 | 35,294 | 34,809 | 30,123 | 27,987 |
| 24 Hour Compression Strength PSI | 72,985 | 79,748 | 77,294 | 82,725 | 81,003 | 81,340 |
| Gamma Two Phase | No | No | No | No | No | No |
| Creep(%) | 0.10 | 0.10 | 0.09 | 0.09 | 0.08 | 0.08 |

EXAMPLE IV

The alloy powders of Example III are annealed at 200° C and 300° C for 75 minutes are mixed with mercury at a mercury to powder ratio of .9:1. Each sample is triturated and the physical properties determined as previously described. The following results are obtained.

TABLE IV

| | 200° C for 75 Min. | 300° C for 75Min. |
|---|---|---|
| Mercury to Powder Ratio | .9:1 | .9:1 |
| Setting Time | 2 min. | 4 min. |
| One Hour Compression Strength PSI | 27,575 | 19,782 |
| 24 Hour Compression Strength PSI | 67,140 | 68,414 |
| Gamma Two Phase | No | No |

EXAMPLE V 852 grams of silver, 550 grams of tin, 496 grams of copper, 80 grams of indium and 22 grams of zinc are mixed and melted together in an electric resistance furnace at 1100° C. The resultant mixture has the following composition: 42.9 percent silver, 29.1 percent tin, 23.9 percent copper, 3.7 percent indium and 0.4 percent zinc. The melt is poured into a 2 inch diameter graphite mold cast and the ingot allowed to cool to room temperature in air. The casted ingot is annealed at 400° C for eight hours and allowed to cool to room temperature in air. The ingot is mounted on a mechanical lathe at a rotating speed of 80 revolutions per minute. The 30° molybdenum steel cutting tool is used to cut the ingot into powder form. The speed of the cutting tool is controlled at 0.00075 inch per revolution. The filings formed are ball milled for 50 minutes and screened through a 400 mesh screen. A less than 400 mesh powder is annealed at 200° C for 75 minutes. The physical properties of the resultant powder are measured. The properties are determined as follows: mercury to powder ration, 1:1; setting time, 5 minutes; one hour compression strength, 35,331 psi; 24 hour compression strength, 80,890 psi; no gamma two phase, and creep at 0.09 percent.

EXAMPLE VI

Ninety-one grams of silver, 57 grams of tin, 50 grams of copper and 2 grams of zinc are melted together in an induction furnace at 1100° C. The composition of the final melt contains 46.8 percent silver, 28.8 percent tin, 24.0 percent copper and approximately 0.4 percent zinc. The liquid metal is poured into a 1 inch diameter graphite mold and quenched to room temperature in water. The resulting ingot is mounted on a mechanical lathe at a rotating speed of 80 rpms. A cutting tool at a 30° angle is used to cut the ingot at a feeding rate of 0.0015 inches per revolution. The filings are ball milled in a stainless steel jar with stainless steel balls for 2½ hours. The powder is screened through a 400 mesh screen. The −400 mesh powder is annealed at 350° C for 2½ to 3 hours. The following table gives the results of evaluating the gamma two phase, set time and compression strength for the alloy of this Example.

TABLE VI

| | −400 Mesh |
|---|---|
| Powder to Mercury Ratio | 1:1 |
| Gamma Two Phase | No |
| Setting Time | ~ 2½ min. |
| One Hour Compression Strength | 24,636 psi |
| 24 Hour Compression Strength | 50,636 psi |

Comparing the compressive strengths of amalgams made from the alloy of this Example VI, which does not contain indium, with the compressive strengths of the amalgams made from the alloys of the previous Examples, which contain indium, clearly indicates the improved strength characteristics of our indium containing alloys of the present invention.

The present invention has been described in terms of presently known preferred embodiments and it is intended the compositions which may depart from those presently preferred which demonstrate the novel advantages of use are to be included in the scope of the appended claims.

What is claimed is:

1. An amalgamatable dental alloy comprising particles with each particle being a homogeneous mixture of 35 to 50 percent silver, 20 to 30 percent copper, 25 to 35 percent tin and 2 to 8 percent indium.

2. A dental alloy according to claim 1 containing from 41 to 46 percent silver.

3. A dental alloy according to claim 1 containing 22 to 25 percent copper.

4. A dental alloy according to claim 1 containing 26 to 29 percent tin.

5. A dental alloy according to claim 1 containing 3 to 5 percent indium.

6. A dental alloy according to claim 1 wherein the particles are less than 325 mesh in size.

7. An amalgamatable dental alloy according to claim 1 containing up to 2 percent zinc.

8. An amalgamatable dental alloy comprising particles having a homogeneous composition of 41 to 46 percent silver, 22 to 25 percent copper, 26 to 29 percent tin and 3 to 5 percent indium.

9. An amalgamatable dental alloy according to claim 8 wherein the particles have a size of less than 400 mesh.

10. A dental alloy according to claim 8 wherein the particles are irregularly shaped particles.

11. A dental alloy according to claim 8 wherein the particles are spherical in shape.

12. A dental alloy according to claim 1 wherein the silver to tin ratio is from 1:1 to 2:1.

13. A dental alloy according to claim 1 wherein the tin to copper ratio is 5/6:1 to 1 3/4:1.

14. A dental alloy according to claim 1 wherein the silver to tin ratio is 1:1 to 2:1 and the tin to copper ratio is 5/6:1 to 1 3/4:1.

* * * * *